US007092529B2

(12) United States Patent
Yu et al.

(10) Patent No.: US 7,092,529 B2
(45) Date of Patent: Aug. 15, 2006

(54) ADAPTIVE CONTROL SYSTEM FOR NOISE CANCELLATION

(75) Inventors: Zhuliang Yu, Singapore (SG); Ming Zhang, Singapore (SG); Hui Lan, Singapore (SG); Susanto Rahardja, Singapore (SG)

(73) Assignee: Nanyang Technological University (SG)

( * ) Notice: Subject to any disclaimer, the term of this patent is extended or adjusted under 35 U.S.C. 154(b) by 586 days.

(21) Appl. No.: 10/285,641

(22) Filed: Nov. 1, 2002

(65) Prior Publication Data

US 2004/0086137 A1 May 6, 2004

(51) Int. Cl.
*A61F 11/06* (2006.01)
*H03B 29/00* (2006.01)
*G10K 11/16* (2006.01)

(52) U.S. Cl. .................................. 381/71.11; 381/71.8

(58) Field of Classification Search ............ 381/71.11, 381/71.1, 71.12, 71.8
See application file for complete search history.

(56) References Cited

U.S. PATENT DOCUMENTS 4,742,548 A 5/1988 Sessler et al.
5,226,076 A 7/1993 Baumhauer, Jr. et al.
5,610,991 A * 3/1997 Janse .......................... 381/92
6,044,068 A * 3/2000 El Malki .................... 370/286
6,625,285 B1 * 9/2003 Ohashi ...................... 381/71.3
6,937,980 B1 * 8/2005 Krasny et al. .............. 704/231
2003/0108214 A1 * 6/2003 Brennan et al. ........... 381/94.7
2003/0206640 A1 * 11/2003 Malvar et al. ................ 381/93

FOREIGN PATENT DOCUMENTS

WO WO 01/95666 A2 12/2001

* cited by examiner

*Primary Examiner*—Vivian Chin
*Assistant Examiner*—Jason Kurr
(74) *Attorney, Agent, or Firm*—Davidson Berquist Jackson & Gowdey, LLP

(57) ABSTRACT

An adaptive noise canceling system for extracting a desired signal, comprising an adaptive noise cancellation filtering circuit for suppressing noise from a first input signal using a second input signal as a reference signal, and generating an output filtered signal representing the desired signal; and an adaptive noise cancellation controller for receiving the first and second input signals and the output filtered signal, and generating an output control signal for controlling coefficients of at least one adaptive filter of the adaptive noise cancellation filtering circuit, comprising a silence detector unit for detecting whether an acoustical signal is present in the input signals and the output filtered signal, and generating a first output signal which indicates whether the acoustical signal is present; a signal detector unit for detecting whether the desired signal is present in the input signals and the output filtered signal, and generating a second output signal which indicates whether the desired signal is present; and an adaptive noise cancellation filter (ANCF) controller unit for receiving the first and second output signal to determine the characteristic of the input signals, and generating the output control signal which represents an updated coefficient parameter for updating the coefficients of the at least one adaptive filter of the adaptive noise cancellation filtering circuit.

9 Claims, 11 Drawing Sheets

ADAPTIVE CONTROL SYSTEM FOR NOISE CANCELLATION

This invention relates to an adaptive noise canceling system. In particular, the invention relates to an adaptive noise cancellation controller to be used in the adaptive noise canceling system.

BACKGROUND OF THE INVENTION

A noise cancellation microphone system is gaining more importance nowadays, especially with the development of multimedia applications and wireless communication technologies. Although various solutions were proposed to enhance desired signal extraction, particularly desired speech, in noisy environments, there are still rooms for improvement in order to obtain a high Signal-to-Noise (SNR) ratio using very few microphones.

Various methods were commonly used to increase the SNR of desired speech signal. In a known speech enhancement method, a single microphone is used to pick up the desired speech signal with noise. The noise spectrum is estimated and subtracted from the speech signal (containing the noise) picked up by the microphone. In this way, the desired speech signal is separated from the noise. However this method is only effective with stationary noise, and also introduces high distortion to the desired speech signal.

Another known noise cancellation method uses two microphones, with one microphone located near the source of the desired signal, and another microphone located near the noise source. Thus, the signal picked up by the microphone arranged near the noise source can be used to adaptively cancel the noise signal contained in the signal picked up by the microphone located near the desired speech signal. However, this method is not practical in most applications as it is very difficult to arrange a microphone near the noise source.

A further known microphone array system uses more than two microphones. The system uses spatial and temporal filtering method to enhance the desired speech signal from a specific direction and over an interested frequency band, and suppress any other signals from other directions. It can enhance the desired signal with a high SNR improvement. However the use of more than two microphones results in a large size of the system, making many mobile applications unsuitable. In the system disclosed in [1], more than three microphones are used to form a uni-directional microphone system for noise cancellation. Since in this system, there are no adaptive signal processing method used, the spatial response of this microphone system is fixed. This makes the whole system inflexible and also results in the performance of noise/interference cancellation to be poor.

Accordingly to the system described in [2], two microphones are used to form a first-order microphone system for noise cancellation. However, this microphone system uses only the differential property of sound field to form a fixed beam pattern, the performance of the system is therefore poor, especially in environments with complicated noise signals.

In the system disclosed in [3], a cardioid-type directional microphone and an omni-directional microphone are combined in an acoustically coupled way. The two microphones, together with an adaptive control circuit, produces a very narrow 3-dimensional beam for acquiring the desired speech signal. However the adaptive filter in the adaptive control circuit uses a normal Least-Mean-Squared (LMS) algorithm with a fixed step size or an adaptive step size which is based on the signal correlation coefficient. Such a method gives rise to performance degradation due to wrong updating of the coefficients of the adaptive filter when speech and noise signal are present simultaneously. This results in low noise suppression and high desired signal cancellation.

Therefore, a noise cancellation microphone system with a high SNR improvement, but is compact in size is desired.

SUMMARY OF THE INVENTION

It is thus an object of the invention to provide a noise cancellation system which is able to provide significant improvement in performance, compared to the existing noise cancellation system, in retaining desired signal and suppressing noise.

The object is achieved by an adaptive noise canceling system according to the invention. The adaptive noise canceling system comprises an adaptive noise cancellation filtering circuit for suppressing noise from a first input signal using a second input signal as a reference signal, and generating an output filtered signal representing the desired signal; and an adaptive noise cancellation controller for receiving the first and second input signals and the output filtered signal, and generating an output control signal for controlling coefficients of at least one adaptive filter of the adaptive noise cancellation filtering circuit, the adaptive noise cancellation controller comprises a silence detector unit for detecting whether an acoustical signal is present in the input signals and the output filtered signal, and generating a first output signal which indicates whether the acoustical signal is present; a signal detector unit for detecting whether the desired signal is present in the input signals and the output filtered signal, and generating a second output signal which indicates whether the desired signal is present; and an adaptive noise cancellation filter controller unit for receiving the first and second output signal to determine the characteristic of the input signals, and generating the output control signal which represents an updated coefficient parameter for updating the coefficients of the at least one adaptive filter of the adaptive noise cancellation filtering circuit.

The adaptive noise canceling filtering circuit of the adaptive noise canceling system can be implemented according to the disclosure in [3]. The adaptive noise cancellation filtering circuit comprises an adaptive filter, which can be implemented using a normal Least-Mean-Squared (LMS) algorithm. According to the invention, an updated coefficient parameter, for example a step size value, of the adaptive filter is controlled by the adaptive noise cancellation controller. The step size value affects the weights or coefficients of the adaptive filter, and hence can be used to update the coefficients of the adaptive filter. The step size is set to a small value by the adaptive noise cancellation controller when a desired signal, in particular a desired speech, is detected. The step size is set to large value when the desired speech is not detected. When no signal is detected (when there is silence), the step size is set to zero and the weights of the adaptive filter remain unchanged, so that the filter can operate properly and stably.

Since the step size value of the adaptive filter used in the adaptive noise canceling system can change in an adaptive manner depending on the type of signals present, it allows the noise cancellation filtering circuit to be able to effectively cancel unwanted noise and remain desired signal.

The first and second input signals result from acoustical signals received by input units, for example microphones.

The acoustical signals can be classified into background noise, interference noise, or desired signal.

The adaptive noise cancellation controller comprises the silent detector unit, the signal detector unit and the adaptive noise cancellation filter (ANCF) controller unit.

The silence detector unit detects whether the first and second input signals and the output filtered signal correspond to a "silent" signal, and generates the first output signal accordingly. In other words, the silence detector unit detects the case when there is no strong background noise, interference signal or any desired signal and generates the first output signal indicating whether such mentioned noise or signal are present. When a "silence" signal is indicated by the first output signal, it means that only random circuit noise such as channel noise is present.

The signal detector unit detects whether the desired signal, in particular desired speech, is present, and generates the second output signal accordingly. The second output signal provides information on whether the desired speech or interference noise, or a combination of both the desired speech and interference noise are present.

The ANCF controller unit receives the first output signal and the second output signal and uses the information thereof to determine the characteristic of the input signals, and generates an appropriate step size value to be used for updating the weights or coefficients of the adaptive filter of the adaptive noise cancellation filtering circuit. The ANCF controller unit then generates the output control signal which corresponds to the appropriate step size value. Since the step size value is a parameter used for updating the weights or coefficients of the adaptive filter, by obtaining an optimal step size value, the updating of the weights or coefficients of the respective filters can be performed more efficiently.

The ANCF controller unit uses a counter based method combined with an adaptive update method to get a stable control on the step size value of the adaptive noise canceling filter. Therefore, a smooth control signal from the ANCF controller is ensured even under uncertain system perturbation. This prevents the adaptive noise canceling system from becoming unstable, and short uncertain perturbation will not affect the performance of the noise canceling system. Furthermore, since the step size of the adaptive filter is not fixed but changes in an adaptive manner, the weights of the filter can be obtained at the optimal value and undesired updating can be avoided even when the input signals change.

The adaptive noise cancellation controller further comprises a power estimator unit for each of the first input signal, the second input signal and the output filtered signal. The power estimator unit generates a power signal corresponding to the estimated power of the received signal.

The output power of the power estimation unit (i.e. power signal) is designed to follow any rapid changes in its input. When the desired signal contained in the input to the power estimation unit fades away, the power signal should decay slowly so that the weights of the adaptive filter of the adaptive noise cancellation filtering circuit are not updated wrongly when the desired signal is present.

The use of signal power information for detecting acoustical signals is more robust and reliable than using the correlation information between input signals.

The adaptive noise cancellation system according to the invention preferably further comprises a post processing filtering circuit which is adapted to receive the first and second input signals, and the output filtered signal. The post processing filtering circuit comprises a Finite Impulse Response (FIR) filter for further removing the noise, hence resulting in the output of the adaptive noise canceling system, a digital result signal, having a higher SNR compared to any existing system.

The step size value of the FIR filter of the post processing filtering circuit may be fixed. According to the preferred embodiment of the invention, the step size value of the FIR filter is controlled by a further output control signal which is generated by a post processing filter (PP) controller unit in the adaptive noise cancellation controller.

The PP controller unit in the adaptive noise cancellation controller receives the first output signal and the second output signal from the silence detector unit and the signal detector unit, respectively, to determine the characteristic of the signals, and to use the information thereof to determine an appropriate step size value to be used for updating the weights or coefficients of the FIR filter of the post processing filtering circuit. The PP filter controller unit is adapted to generate the further output control signal which corresponds to the appropriate step size value for the FIR filter of the post processing filtering circuit.

The PP filter controller unit also uses a counter based method combined with an adaptive update method to get a stable control on the step size parameters of the adaptive filter of the PP filtering circuit.

Since the step size value of the adaptive filter used in the PP filtering circuit changes in an adaptive manner according to the input signals, the digital result signal generated by the filtering circuit has a higher average SNR than in the case when the step size value is fixed.

The adaptive noise canceling system is preferably implemented in an adaptive directional noise canceling microphone system comprising an omni-directional microphone having a first directivity pattern, thereby providing a similar gain for sounds at least from the first direction and from a second direction; and a directional microphone having a second directivity pattern, thereby providing a higher gain for sounds coming from the first direction than for sounds coming from the second direction; the omni-directional microphone and the directional microphone being arranged in a closely acoustically-coupled way. The adaptive noise canceling microphone system as described above receives signals resulting from the sounds received by the microphones, and generates the digital result signal representing the desired signal using the adaptive noise canceling system according to the invention as described above.

The microphone system according to the invention is able to form a 3-dimensional beam. Sounds detected within the 3-dimensional beam are considered as desired signal, and sounds detected outside the beam are considered as noise or interference. The width of the 3-dimensional beam can be adjusted for different applications. The microphone system according to the invention can be used to acquire any kind of sounds and to suppress stationary or non-stationary noise/interference, including speech and music.

A first amplifier and a second amplifier are used to amplify the signals resulting from the sounds picked up by the omni-directional and directional microphones, respectively. The amplified signals are filtered by a first and second low pass filter to generate analog amplified and filtered signals. The analog amplified and filtered signals are converted to digital signals using a first and second Analog-to-Digital (A/D) converter, the digital signals are the first and second input signals which are inputs to the adaptive noise canceling system.

The adaptive noise canceling system processes the input signals and produces the digital result signal representing the desired signal, which can be further processed if desired. To use the digital output in most analog devices, such as speakers, an Analog-to-Digital (A/D) converter can be used to convert the digital result signal into a result signal output, which is an analog signal. The result signal output can then be used as input signal to any equipment, for example, a speaker.

DETAILED DESCRIPTION OF THE INVENTION

The invention will now be described with reference to the accompanying drawings.

The adaptive noise canceling system according to the invention is preferably implemented in an adaptive directional noise canceling microphone (ADNCM) system for retaining desired signal, in particular desired speech, and suppressing unwanted signals.

Figure 1:
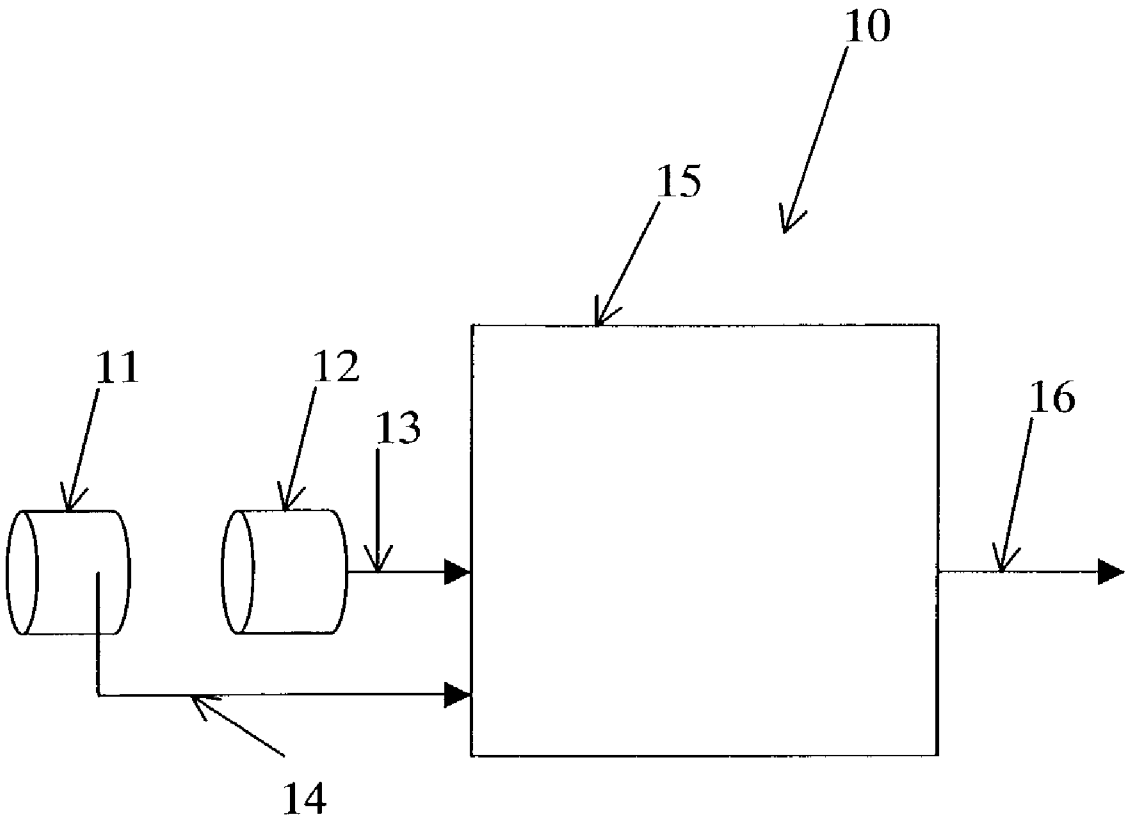
FIG. 1 shows the block diagram of an adaptive directional noise cancellation microphone system, comprising a processing unit according to the invention.

FIG. 1 shows a block diagram of an ADNCM system 10 in which the adaptive noise canceling system is implemented. An uni-directional microphone 11, preferably a cardioid-type direction microphone is arranged close to an omni-directional microphone 12, such that both microphones 11,12 are acoustically coupled with each other. The uni-directional microphone 11 and the omni-direction microphone 12 generate signals 13,14 resulting from sounds received. The signals 13,14 are received by a processing unit 15, and a result signal output 16 is generated by the processing unit 15.

The uni-directional microphone 11 and the omni-directional microphone 12, together with a digital signal processing method developed specially for this purpose, forms a 3-dimensional beam directed towards a desired direction. Sounds coming from a region within the 3-dimensional cone beam are considered as desired signal, and sounds coming from outside the cone beam are considered as noise or interference signal.

Figure 2:
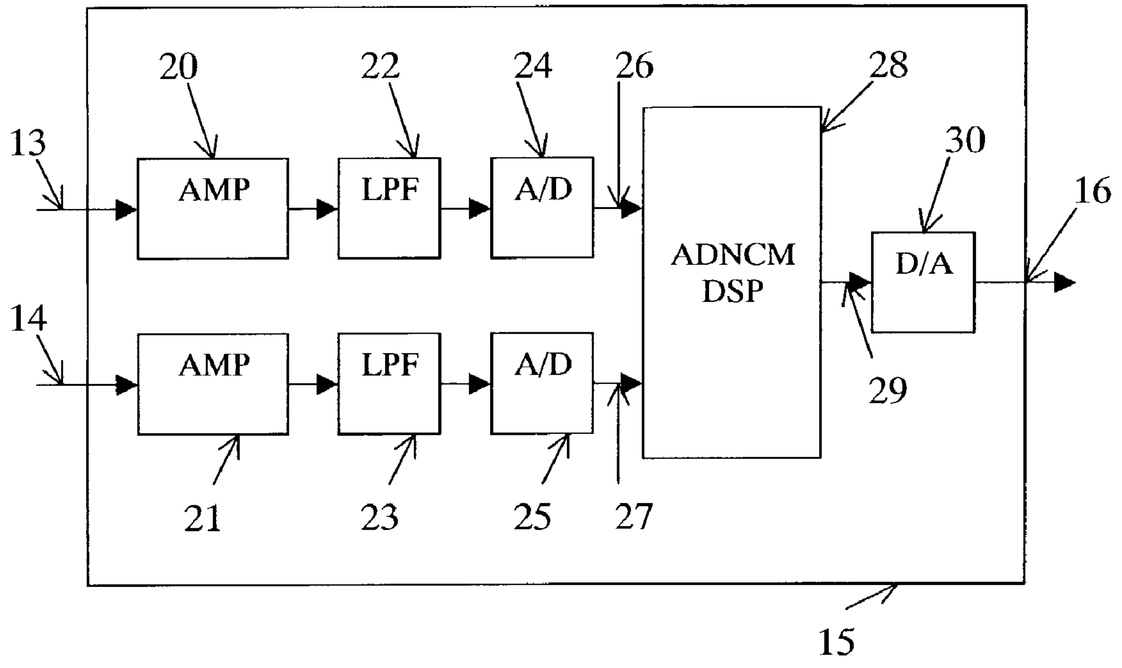
FIG. 2 shows the block diagram of the processing unit according to the invention.

FIG. 2 shows the block diagram of the processing unit 15. The signals 13,14 generated by the microphones 11,12 are amplified in a first amplifier 20 and a second amplifier 21, respectively. The amplified signals are filtered in a first and second low pass filter 22,23 to remove any high frequency components. The amplified and filtered signals are subsequently converted to digital signals 26,27 using a first and second Analog-to-Digital (A/D) converters 24,25 which digital signals 26,27 are to be processed by the adaptive noise canceling system 28.

The digital signals 26,27 are received as input signals by the adaptive noise canceling system 28 for processing, so that desired signal is remained and enhanced, and the noise or interference signal are cancelled. The output of the adaptive noise canceling system 28 is a digital result signal 29. The digital result signal 29 can be further processed by other systems, or converted to an analog signal for driving output devices like speakers. According to the invention, the digital result signal 29 is converted to an analog signal, known as the result signal output 16, using a Digital-to-Analog (A/D) converter.

Figure 3:
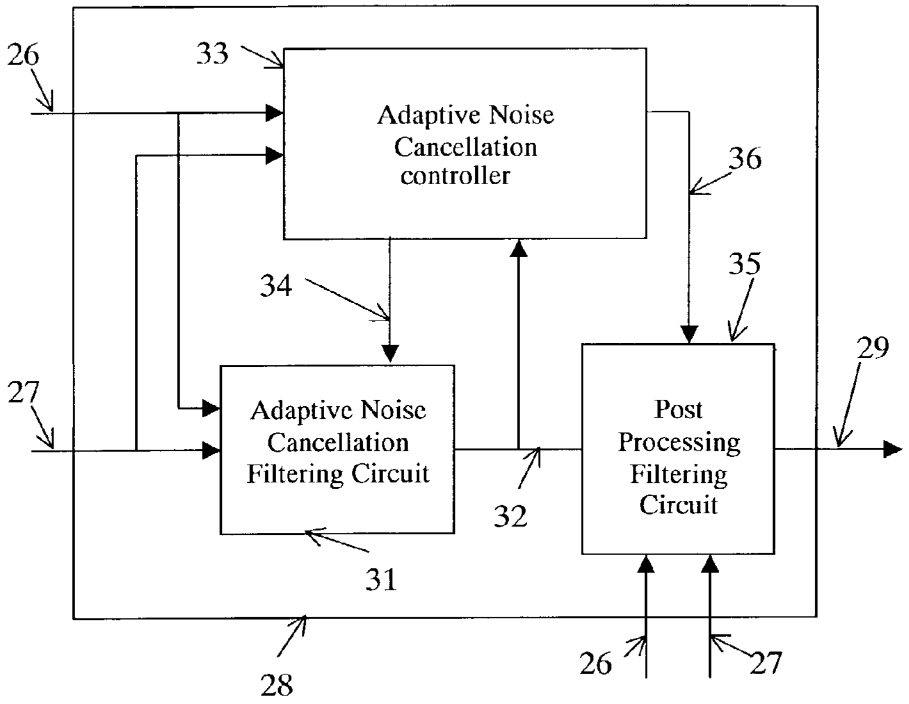
FIG. 3 shows the detail block diagram of the adaptive noise canceling system according to the invention.

FIG. 3 shows the block diagram of the adaptive noise canceling system 28 according to the invention. The adaptive noise canceling system 28 comprises an adaptive noise cancellation filtering circuit 31, an adaptive noise cancellation controller 33 and a post processing filtering circuit 35. The adaptive noise cancellation filtering circuit 31 receives the input signals 26,27 and an output control signal 34 from the adaptive noise cancellation controller 33, and generates an output filtered signal 32. The post processing filtering circuit 35 is adapted to receive the input signals 26,27, the output filtered signal 32 and a further output control signal 36 from the adaptive noise cancellation controller 33, and to generate the digital result signal 29.

The adaptive noise cancellation controller 33 receives the input signals 26,27 and the output filtered signal 32, and generates the output control signal 34 and the further output control signal 36 for controlling the adaptive noise cancellation filtering circuit 31 and the post processing filtering circuit 35, respectively.

The adaptive noise cancellation controller 33 controls both the adaptive noise cancellation filtering circuit 31 and the post processing filtering circuit 35 by updating the step size value of the coefficients of the filters in both the filtering circuits 33,35.

Figure 4:
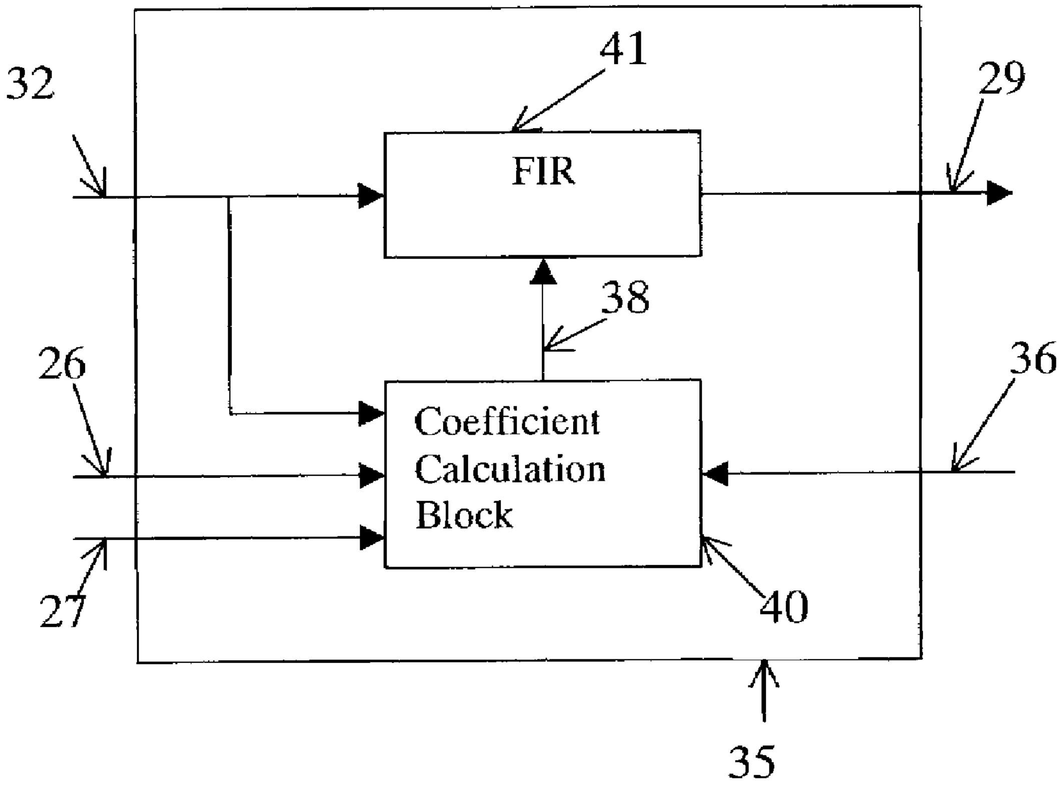
FIG. 4 shows the detail block diagram of the post processing filter circuit according to the invention.

The adaptive noise cancellation filtering circuit 31 is preferably implemented according to the disclosure in [3], and the post processing filtering circuit 35 is preferably implemented as shown in FIG. 4.

Figure 5:
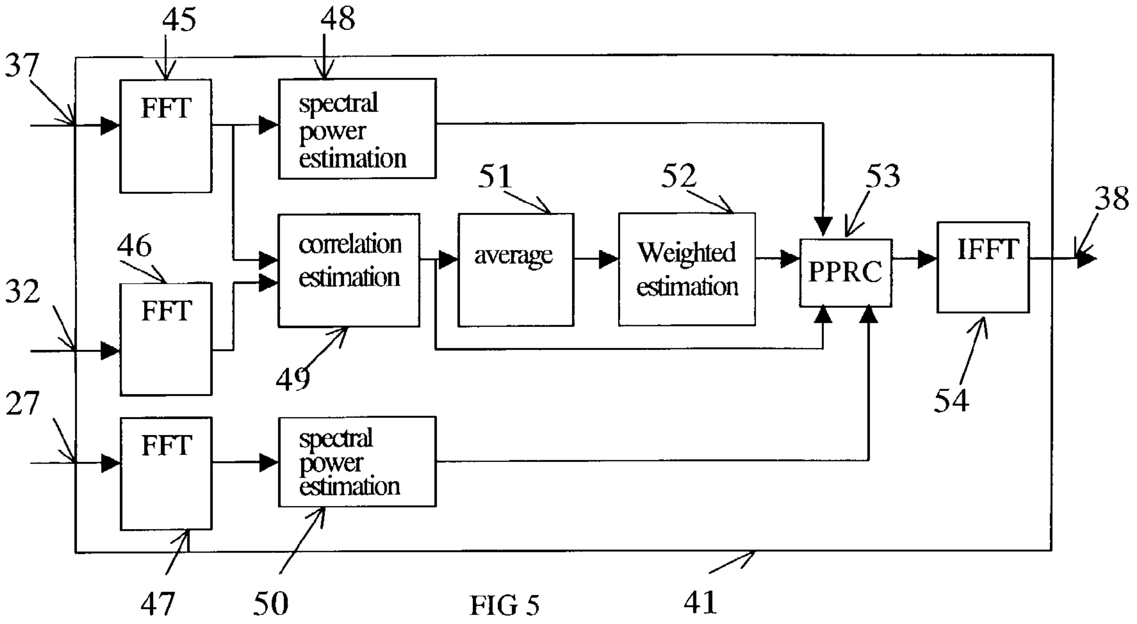
FIG. 5 shows the detail block diagram of the post processing unit.

FIG. 4 shows the post processing filtering circuit 35 according to the preferred embodiment of the invention. The post processing filtering circuit 35 comprises a Finite Impulse Response (FIR) filter 41 and a coefficient calculation block 40. The FIR filter 41 receives the output filtered signal 32 and further reduces any noise present in the output filtered signal 32 to generate the digital result signal 29. The coefficients for the FIR filter 41 are updated by copying coefficients determined from the coefficient calculation block 40. The coefficient calculation block 40 receives the first input signal 26, the second input signal 27 and the output filtered signal 32 as references, together with the further output control signal 36 as the step size value, to generate the coefficients to be used as the coefficients for the FIR filter 41. The detailed implementation of the coefficient calculation block 40 can be summarized in FIG. 5.

The delayed signal 37 is input into a Fast Fourier Transform (FFT) circuit 45 to transform the delayed signal 37 into the frequency domain. Similarly, the second input signal 27 and the output filtered signal 32 are also received by separate FFT circuits 46,47 and transformed into their counterparts in the frequency domain. The frequency counterparts of the delayed signal 37 and second input signal 27 are received by two separate spectral power estimation circuits 48,50 for generating corresponding power signals. The frequency counterparts of the delayed signal 37 and second input signal 27 are also received by a correlation estimation circuit 49 to generate a correlation signal, wherein the correlation signal is received by an averager 51 to generate an averaged correlation signal.

The averaged correlation signal is then input into a weight estimation circuit 52 to generate a weight signal. The weight signal, correlation signal and the two power signals generated from the spectral power estimation circuits 48,50 are used as inputs to a post processing response calculator (PPRC) 53. The output of the post processing response calculator (PPRC) 53 represents the frequency response of the post processing filter 41 in the frequency domain. The output of the post processing response calculator (PPRC) 53 is received by an Inversed-FFT circuit 54 to generate a coefficient signal 38, representing the coefficients of the filter 41 in the time domain. The time domain coefficients (or coefficient signal 38) are copied to the post processing filter 41 to further suppress unwanted noise and generate the digital result signal 29.

Figure 6:
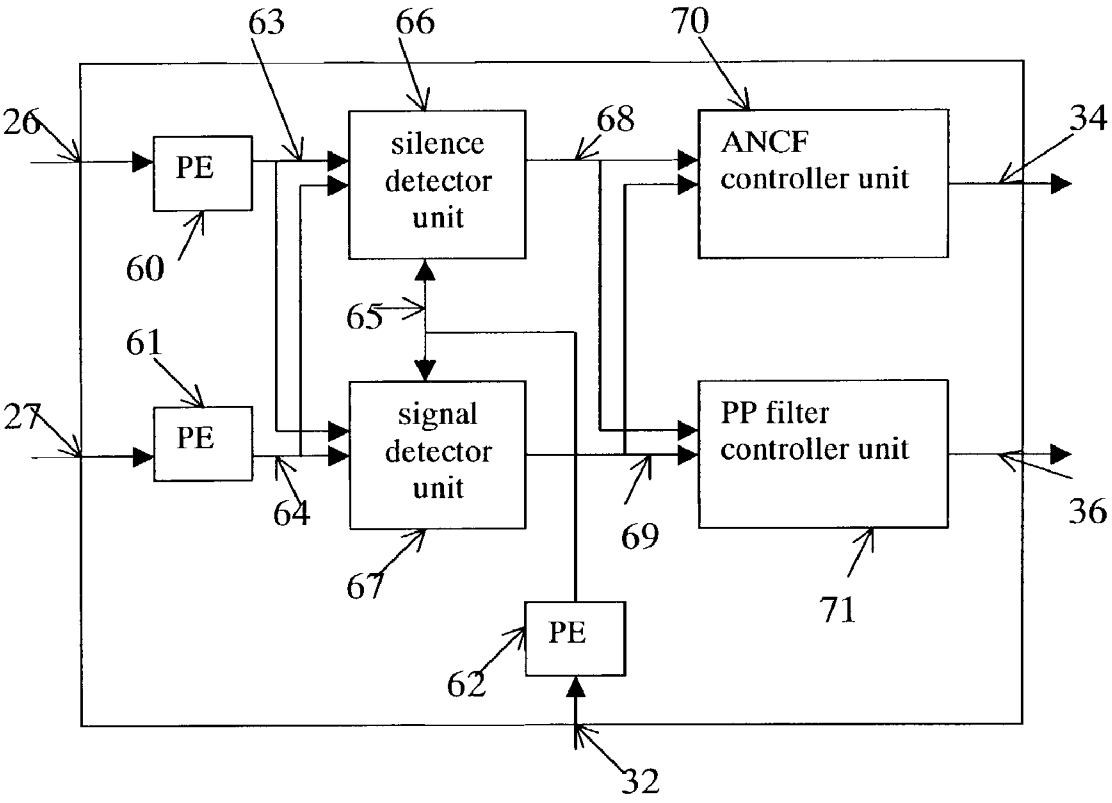
FIG. 6 shows the detail block diagram of the adaptive noise cancellation controller according to the invention.

FIG. 6 shows the block diagram of the adaptive noise cancellation controller 33 according to the invention. The adaptive noise cancellation controller 33 comprises three power estimator units 60,61,62, a silence detector unit 66, a signal detector unit 67, an adaptive noise canceling filter (ANCF) controller 70 and a post processing (PP) filter controller 36.

The three power estimator units 60,61,62 are used to estimate the power of the three input signals 26,27,32. The outputs of the power estimator are three power signals 63,64,65. The power signals 63,64,65 are received as inputs by both the silence detector unit 66 and the signal detector unit 67. The silence detector unit 66 generates a first output signal 68, and the signal detector unit 67 generates a second output signal 69. The ANCF controller receives both the first and second output signal 68,69 and generates the output control signal 34. Similarly, the PP filter controller 71 receives the first and second output signal 68,69 and is adapted to generate the further control signal 36.

The output control signal 34 and the further output control signal 36 are used to control the step size value of the adaptive filter of the adaptive noise cancellation filtering circuit and the FIR filter of the post-processing filtering circuit, respectively.

Figure 7:
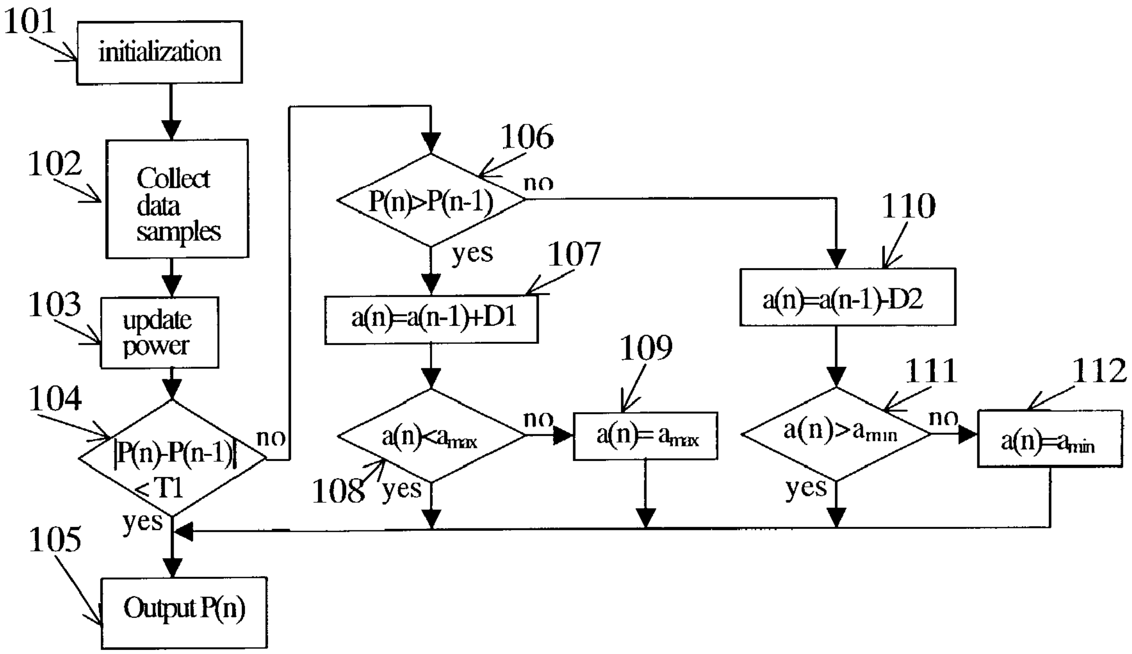
FIG. 7 shows the flow diagram of a power estimator unit according to the invention.

FIG. 7 shows a flow chart of any of the power estimator units 60,61,62. At an initialization step 101, the initial power of the input signals 63,64,65 are initialized to zero:

$$p_1(n),\ p_2(n),\ p_3(n)=0 \tag{1}$$

wherein $p_1(n)$, $p_2(n)$ and $p_3(n)$ are the power of the input signals 26,27,32, respectively, corresponding to the power signals 63,64,65.

Similarly, the initial power update forgetting factors of the power estimators 60,61,62 are also initialized to some nonzero value:

$$a_1(n),\ a_2(n),\ a_3(n)=0.5 \tag{2}$$

wherein $a_1(n)$, $a_2(n)$ and $a_3(n)$ are the power update forgetting factors of power estimators 60,61,62, respectively. The minimum value of the power update forgetting factors is $a_{min}$ and the maximum value is $a_{max}$.

After the initialization step 101, the input signals 26,27,32 are collected at step 102. The power of each of the input signals 26,27,32 are then updated in step 103 using the following formula:

$$p(n)=(1-a(n))*p(n-1)+a(n)*|x(n)|^2 \tag{3}$$

wherein x(n) is any of the input signals 26,27,32, p(n) is the current power of any of the input signals $p_1(n)$, $p_2(n)$ or $p_3(n)$, and p(n−1) is the previous power.

In step 104, the value of the current power P(n) is compared with a value of the previous power P(n−1) before updating to determine whether the power P(n) of the corresponding input signal is stationary. The comparison of the current power P(n) and previous power P(n−1) is performed using the following formulae:

$$D_p=|p(n)-p(n-1)| \tag{4}$$

$$D_p<T_1 \tag{5}$$

wherein $T_1$ is a parameter which is used to determine whether the estimated signal power is stable. When $D_p$ is smaller than $T_1$, it means that the power P(n) of the input signal is substantially stationary. In this case, the power P(n) is generated as the output power of the input signal in step 105.

When $D_p$ is greater than $T_1$, it means that the power of the input signal has large change between the current power P(n) and previous power P(n−1), and the power estimator unit then compares the power values in step 106, using the following:

$$p(n)>p(n-1) \tag{6}$$

If p(n) is greater than p(n−1), the power estimator unit updates the power updating factor a(n) in step 107 using the following formula:

$$a(n)=a(n-1)+D_1 \tag{7}$$

wherein a(n) is the current power updating factor $a_1(n)$, $a_2(n)$, $a_3(n)$ of any of the power estimator unit 60,61,62, a (n−1) is the previous power updating factor, and $D_1$ is a positive step size parameter for updating the power updating factor a(n).

The updated power updating factor a (n) is further compared in step 108 to determine whether it exceeds a maximum value:

$$a(n)<a_{max} \tag{8}$$

wherein $a_{max}$ is the maximum allowable value of a(n). If a(n) is smaller than $a_{max}$, the power p(n) is generated as the output power in step 105. If a(n) is greater than $a_{max}$, then a(n) is assigned the value of $a_{max}$ in step 109 and the power p(n) is generated as the output power in step 105.

If p(n) is determined to be smaller than p(n−1) during comparison in step 106, the power estimator unit updates the power updating factor a(n) in step 110 using the following formula:

$$a(n)=a(n-1)-D_2 \tag{9}$$

and determines in step 111 whether a(n) is greater $a_{min}$:

$$a(n)>a_{min} \tag{10}$$

wherein $D_2$ is another step size parameter for updating the power updating factor a(n), and $a_{min}$ is a minimum allowable value of a(n). If a(n) is greater than $a_{min}$, the power p(n) is generated as the output power in step 105. If a(n) is smaller than $a_{min}$, then a(n) is assigned the value of $a_{min}$ in step 112 and the power p(n) is generated in step 105.

Figure 8:
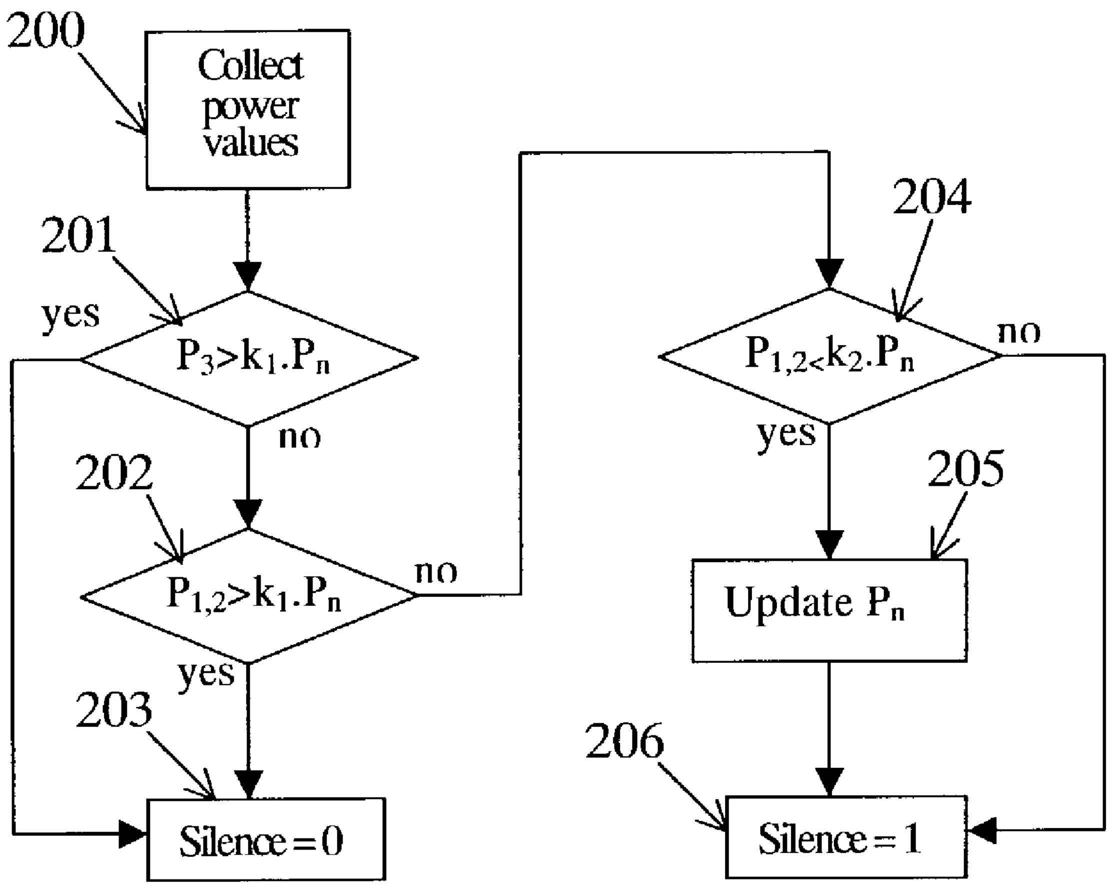
FIG. 8 shows the flow diagram of the silence detector unit according to the invention.

The power p(n) generated from step 105 is used as the output power for the silence detector unit 66 and the signal detector unit 67. The silence detector unit 66 receives the power signals $p_1(n)$, $p_2(n)$ and $p_3(n)$ 63,64,65 as inputs from the respective power estimator units 60,61,62 in step 200 of the flow chart shown in FIG. 8.

In step 201, the power signal $p_3(n)$ 65 from the power estimator unit 62 corresponding to the input signal 32 is compared with the noise power $p_n(n)$:

$$p_3(n)>k_1.p_n(n) \tag{11}$$

wherein $k_1$ is a threshold value used to detect "silence". If $p_3(n)$ is greater than $k_1.p_n(n)$, the "silence" is set to "0" in step 203, indicating that "silence" is not detected, and interference signal and/or desired signal is present. If $p_3(n)$ is smaller than $k_1.p_n(n)$, the silence detector unit checks if both $p_1(n)$ and $p_2(n)$ are greater than $k_1.p_n(n)$ in step 202:

$$p_1(n)>k_1.p_n(n) \tag{12}$$

$$p_2(n)>k_1.p_n(n) \tag{13}$$

If both $p_1(n)$ and $p_2(n)$ are greater than $k_1.p_n(n)$, then "silence" is set to "0" in step 203, else it checks if both $p_1(n)$ and $p_2(n)$ are smaller than $k_2.p_n(n)$ in step 204:

$$p_1(n)<k_2.p_n(n) \tag{14}$$

$$p_2(n)<k_2.p_n(n) \tag{15}$$

wherein $k_2$ is another threshold value used to detect "silence". If both $p_1(n)$ and $p_2(n)$ are smaller than $k_2.p_n(n)$, then the noise power $p_n(n)$ is updated in step 205 using the following formula:

$$p_n(n) = dp_n(n-1) + \frac{(1-d)\cdot(p_1(n)+p_2(n))}{2} \tag{16}$$

wherein d is a fixed parameter which can be selected as 0.9999 for smoothing the background power value. The "silence" is set to "1", indicating that there are no signal present. If in step 204, either one or both of $p_1(n)$ and $p_2(n)$ are greater than $k_2.p_n(n)$, the "silence" is set to "1" directly in step 206 without updating the value of the noise power $p_n(n)$.

Figure 9:
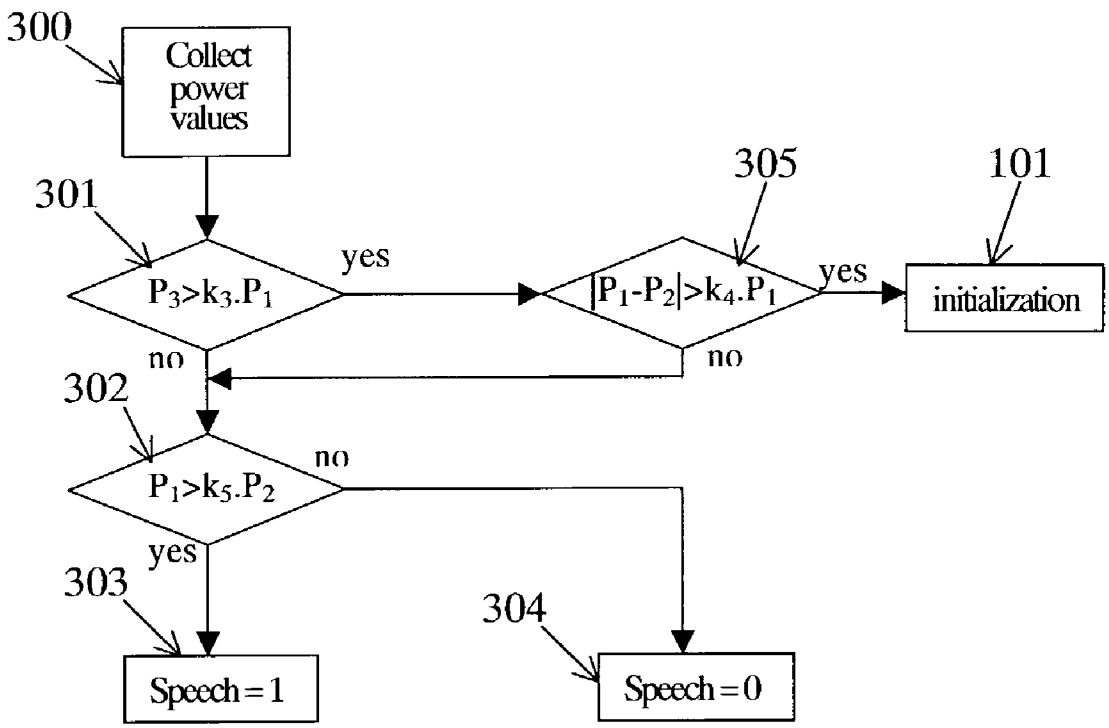
FIG. 9 shows the flow diagram of the signal detector unit according to the invention.

FIG. 9 shows a flow chart of the signal detector unit 67 for also receiving the power signals $p_1(n)$, $p_2(n)$ and $p_3(n)$ 63,64,65 as inputs from the respective power estimator units 60,61,62 in step 300.

In step 301, the power signal $p_3(n)$ is compared with $p_1(n)$:

$$p_3(n)>k_3.p_1(n) \tag{17}$$

wherein $k_3$ is a first threshold value for detecting the desired signal. If $p_{3(n)}$ is smaller than $k_3.p_1(n)$, then the signal detector unit determines in step 302 if:

$$p_1(n)>k_5.p_2(n) \tag{18}$$

wherein $k_5$ is a second threshold value for detecting desired signal. If $p_1(n)$ is greater than $k_5.p_2(n)$, the "signal" is set to "1" in step 303, indicating that desired signal is present. If $p_1(n)$ is smaller than $k_5.p_2(n)$, the "signal" is set to "0" in step 304, indicating that desired signal is not present.

If in step 301, $p_{3(n)}$ is greater than $k_3.p_1(n)$, then the signal detector unit determines further in step 305 if:

$$|p_1(n)-p_2(n)|<k_4.p_1(n) \tag{19}$$

wherein $k_4$ is a third threshold value for detecting the desired signal. If $|p_1(n)-p_2(n)|$ is smaller than $k_4.p_1(n)$, the adaptive noise cancellation system 33 returns to the initialization state in step 101, and all system variables are initialized to the initial values. Otherwise the system 33 proceeds to step 302.

The output of the silence and signal detector units 66,67 are the values of "silence" and "signal", respectively. Knowing the values of "silence" and "signal" enables one to determine whether the signal contained by the input signals 26,27,32 comprises the desired signal, the interference signal or noise, or a combination of them.

The outputs from both the silence detector unit 66 and the signal detector unit 67 are received by the ANCF controller 70 and the PP filter controller 71.

Figure 10:
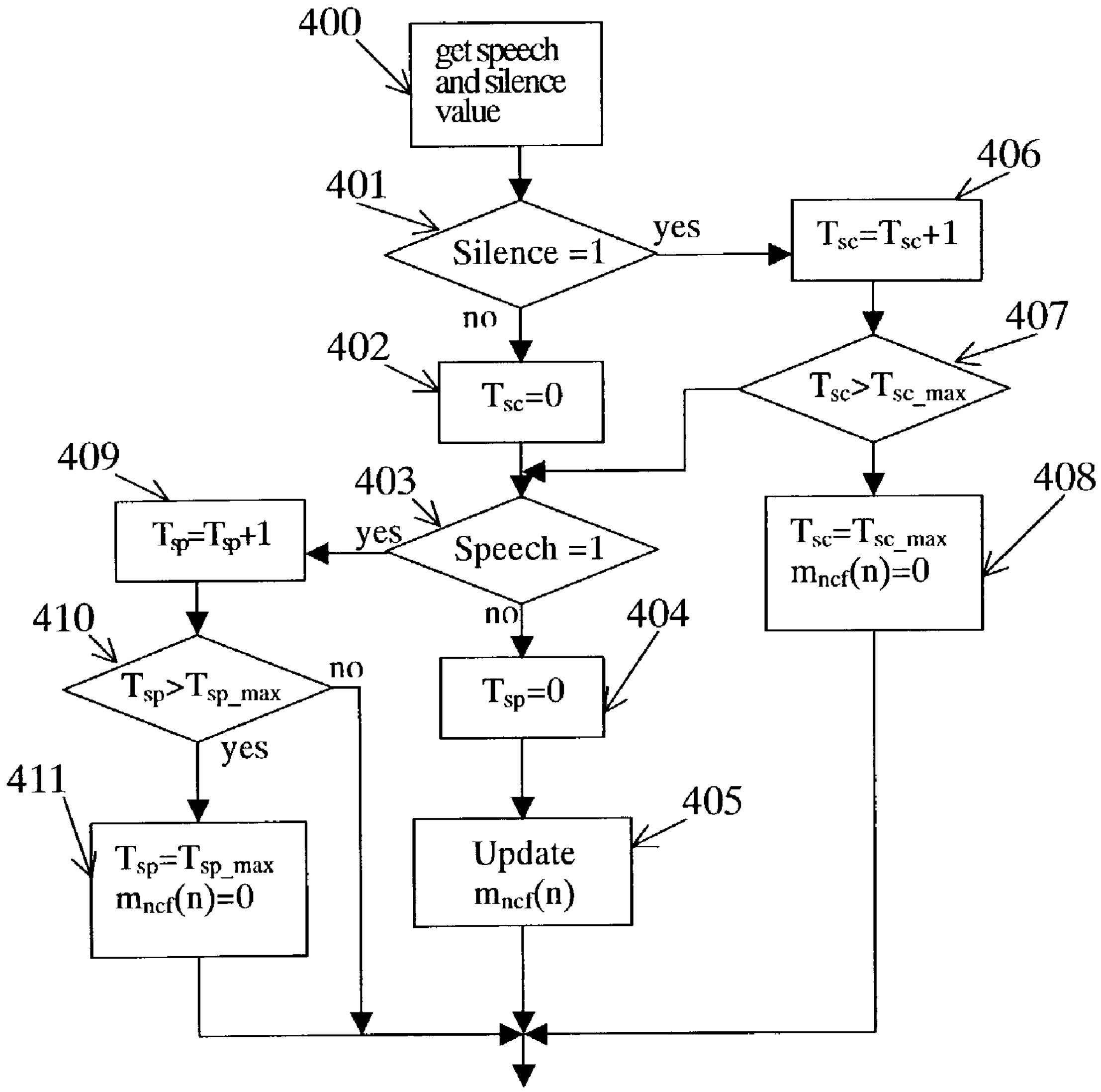
FIG. 10 shows the flow diagram of the adaptive noise cancellation filter controller unit according to the invention.

The flow chart of the ANCF controller 70 is shown in FIG. 10. In step 400, the output from the silence and signal detector units 66,67 are received by the ANCF controller 70. In step 401, the value of "silence" is determined if it is set at "1". If "silence" is not set at "1", i.e. set at "0", then $T_{sc}$ is initialized to 0 in step 402:

$$T_{sc}=0 \tag{20}$$

wherein $T_{sc}$ is a counter for determining "silence" in the ANCF controller 70.

In step 403, the value of "speech" is determined if it is set at "1". If "speech" is not set at "1", then $T_{sp}$ is to 0 in step 404:

$$T_{sp}=0 \tag{21}$$

wherein $T_{sp}$ is a counter for determining "speech" in the ANCF controller 70. The step size parameter for the adaptive filter of the adaptive noise cancellation filtering circuit 31 generated by the ANCF controller 70 is the updated in step 405 using the following formula:

$$m_{ncf}(n)=(1-q).m_{ncf}(n-1)+q \tag{22}$$

wherein $m_{ncf}(n)$ is the step size parameter.

If "silence" is detected to be set at "1" in step 401, then $T_{sc}$ is increment by 1 in step 406:

$$T_{sc}=T_{sc}+1 \tag{23}$$

and the incremented value of $T_{sc}$ is compared to see if it exceeds the maximum value $T_{sc\_max}$ in step 407:

$$T_{sc}>T_{sc\_max}. \tag{24}$$

If $T_{sc}$ is greater than $T_{sc\_max}$, $T_{sc}$ is set to $T_{sc\_max}$, and the output of the ANCF controller 70, $m_{ncf}(n)$, is set to "0" in step 408. Else, the ANCF controller 70 continues to determine the value of "speech" in step 403.

When the "speech" is set "1", $T_{sp}$ is increment by 1 in step 409:

$$T_{sp}=T_{sp}+1 \tag{25}$$

and the incremented value of $T_{sp}$ is compared to see if it exceeds the maximum value $T_{sp\_max}$ in step 410:

$$T_{sp}>T_{sp\_max}. \tag{26}$$

If $T_{sp}$ is greater than $T_{sp\_max}$, $T_{sp}$ is set to $T_{sp\_max}$, and the output of the ANCF controller 70, $m_{ncf}(n)$, is set to "0" in step 411. Else, the output, $m_{ncf}(n)$, remains unchanged.

Figure 11:
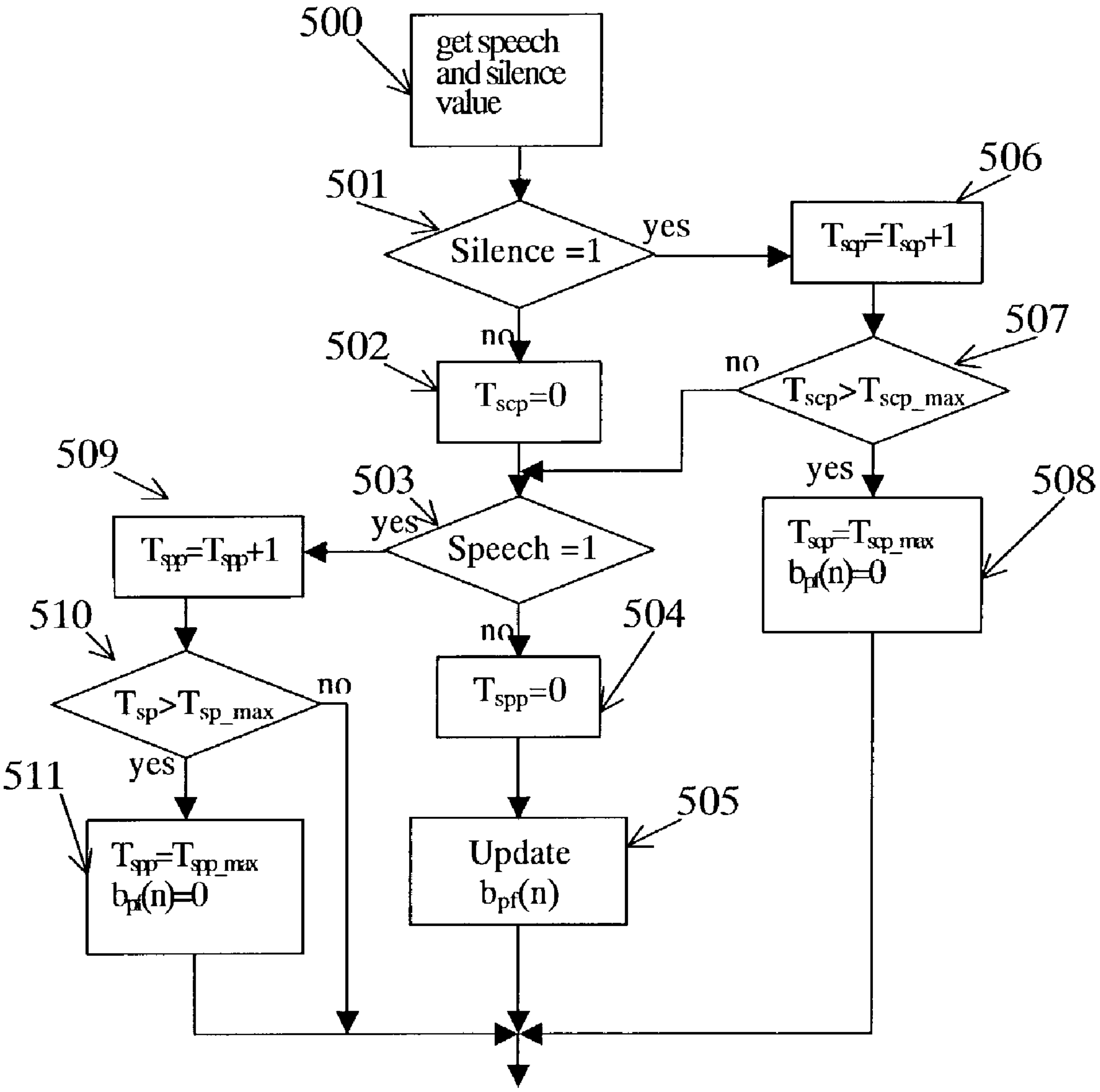
FIG. 11 shows the flow diagram of the post processing filter controller unit according to the invention.

The flow chart of the PP filter controller 71 is shown in FIG. 11. Similarly, the output from the silence and signal detector units 66,67 are received by the PP filter controller 71 in step 500. In step 501, the value of "silence" is determined if it is set at "1". If "silence" is not set at "1", i.e. set at "0", then $T_{scp}$ is initialized to "0" in step 502:

$$T_{scp}=0 \quad (27)$$

wherein $T_{scp}$ is a counter for determining "silence" in the PP filter controller 71.

In step 503, the value of "speech" is determined if it is set at "1". If "speech" is not set at "1", then $T_{spp}$ is to "0" in step 504:

$$T_{spp}=0 \quad (28)$$

wherein $T_{spp}$ is a counter for determining "speech" in the PP filter controller 71. The step size parameter for a noise canceling filter generated by the PP filter controller 71 is the updated in step 505 using the following formula:

$$b_{ncf}(n)=(1-j).b_{ncf}(n-1)+j \quad (29)$$

wherein $b_{ncf}(n)$ is the step size parameter.

If "silence" is detected to be set at "1" in step 501, then $T_{scp}$ is increment by 1 in step 506:

$$T_{scp}=T_{scp}+1 \quad (30)$$

and the incremented value of $T_{scp}$ is compared to see if it exceeds the maximum value $T_{scp\_max}$ in step 507:

$$T_{scp}>T_{scp\_max}. \quad (31)$$

If $T_{scp}$ is greater than $T_{scp\_max}$, $T_{scp}$ is set to $T_{scp\_max}$, and the output of the PP filter controller 71, $b_{ncf}(n)$, is set to "0" in step 508. Else, the PP filter controller 71 continues to determine the value of "speech" in step 503.

When the "speech" is set "1", $T_{spp}$ is increment by 1 in step 509:

$$T_{spp}=T_{spp}+1 \quad (32)$$

and the incremented value of $T_{spp}$ is compared to see if it exceeds the maximum value $T_{spp\_max}$ in step 510:

$$T_{spp}>T_{spp\_max}. \quad (33)$$

If $T_{spp}$ is greater than $T_{spp\_max}$, $T_{spp}$ is set to $T_{spp\_max}$, and the output of the PP filter controller 71, $b_{ncf}(n)$, is set to "0" in step 511. Else, the output, $b_{ncf}(n)$, remains unchanged.

While the embodiments of the invention have been described, they are merely illustrative of the principles of the invention. Other embodiments and configurations may be devised without departing from the spirit of the invention and the scope of the appended claims.

The following documents are used in this specification:

[1] U.S. Pat. No. 4,742,548

[2] U.S. Pat. No. 5,226,076

[3] WO 0,195,666

What is claimed is:

1. An adaptive noise canceling system for extracting a desired signal, comprising an adaptive noise cancellation filtering circuit for suppressing noise from a first input signal using a second input signal as a reference signal, and generating an output filtered signal representing the desired signal; and an adaptive noise cancellation controller for receiving the first and the second input signals and the output filtered signal, and generating an output control signal for controlling coefficients of at least one adaptive filter of the adaptive noise cancellation filtering circuit, comprising a silence detector unit for receiving signals respectively derived from the first input signal, the second input signal and the output filtered signal, detecting whether an acoustical signal is present in the input signals and the output filtered signal using the received signals, and generating a first output signal which indicates whether the acoustical signal is present;

a signal detector unit for receiving signals respectively derived from the first input signal, the second input signal and the output filtered signal, detecting whether the desired signal is present in the input signals and the output filtered signal using the received signals, and generating a second output signal which indicates whether the desired signal is present; and an adaptive noise cancellation filter (ANCF) controller unit for receiving the first and the second output signals to determine the characteristic of the input signals, and generating the output control signal which represents an updated coefficient parameter for updating the coefficients of the at least one adaptive filter of the adaptive noise cancellation filtering circuit.

2. The adaptive noise canceling system according to claim 1, wherein the adaptive noise cancellation controller further comprises a power estimator unit for receiving each of the input signals and the output filtered signal, and generates a power signal corresponding to each of the estimated power of the input signals and the output filtered signal, the power signal to be received by the silence detector unit and the signal detector unit.

3. The adaptive noise canceling system according to claim 1, further comprising a post processing filtering circuit for reducing noise from the output filtered signal, wherein the post processing filtering circuit is adapted to receive the first and the second input signals, the output filtered signal and to generate a coefficient signal to be used as the coefficients of at least one filter, such that the at least one filter is able to reduce noise from the output filtered signal and to generate a digital result signal representing the noise reduced desired signal.

4. The adaptive noise canceling system according to claim 3, wherein the adaptive noise cancellation controller further comprises a post processing filter controller unit for receiving and processing the first and the second output signal signals to determine the characteristic of the first and the second input signals, the post processing controller unit being adapted to generate a further output control signal which represents an updated coefficient parameter for updating the coefficients of the at least one filter of the post processing filtering circuit.

5. An adaptive directional noise canceling microphone system, comprising an omni-directional microphone having a first directivity pattern, thereby providing a similar gain for sounds at least from a first direction and from a second direction; and a directional microphone having a second directivity pattern, thereby providing a higher gain for sounds from the first direction than the second direction; the omni-directional microphone and the directional microphone being arranged in a closely acoustically-coupled way; and the adaptive noise canceling system according to any one of claims 1 to 4 for receiving signals resulting from the sounds received by the omni-directional microphone and the directional microphones, and for generating the digital result signal representing sounds from the first direction with the sounds from the second direction suppressed.

6. The adaptive directional noise canceling microphone system according to claim 5, further comprising a first and a second amplifier for receiving and amplifying the signals resulting from the sounds received by the omni-directional microphone and the directional microphones.

7. The adaptive directional noise canceling microphone system according to claim 6, further comprising a first and a second low pass filter for receiving and filtering the amplified signals from the first and the second amplifiers, thereby generating analog amplified and filtered signals.

8. The adaptive directional noise canceling microphone system according to claim 7, further comprising a first and a second Analog-to-Digital converter for receiving and converting the analog amplified and filtered signals from the first and the second low pass filters to digital signals, thereby generating the first and the second input signals.

9. The adaptive directional noise canceling microphone system according to claim 5, further comprising a Digital-to-Analog converter for receiving and converting the digital result signal to an analog signal, thereby generating an result signal output.

* * * * *